United States Patent [19]

Cho et al.

[11] 4,160,827
[45] Jul. 10, 1979

[54] METRONIDAZOLE PHOSPHATE AND SALTS

[75] Inventors: Moo J. Cho; John J. Biermacher, both of Kalamazoo, Mich.

[73] Assignee: The Upjohn Company, Kalamazoo, Mich.

[21] Appl. No.: 875,393

[22] Filed: Feb. 6, 1978

[51] Int. Cl.² ............... A61K 31/675; A61K 31/685; C07F 9/58; C07F 9/65
[52] U.S. Cl. ................... 424/199; 260/299; 424/200; 544/370; 548/338
[58] Field of Search ............ 260/268 K, 299; 424/199, 200; 548/338

[56] References Cited

U.S. PATENT DOCUMENTS

| | | | |
|---|---|---|---|
| 2,944,061 | 7/1960 | Jacob et al. | 548/338 |
| 3,696,116 | 10/1972 | Jeanmart et al. | 548/338 |
| 3,723,453 | 3/1973 | Gradnik et al. | 548/338 |
| 3,882,136 | 5/1975 | Levon | 260/299 |
| 3,910,945 | 10/1975 | Kreider | 548/338 X |

FOREIGN PATENT DOCUMENTS

571291 3/1959 Belgium .................... 548/338

*Primary Examiner*—Richard Raymond
*Attorney, Agent, or Firm*—John J. Killinger

[57] ABSTRACT

This invention relates to novel compounds of the formula:

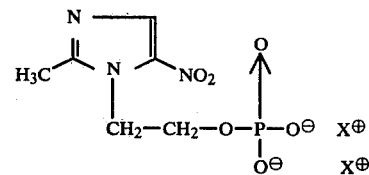

wherein X⊕ is a pharmacologically acceptable cation.

The compounds are water soluble and are compounded with pharmaceutical carriers to form compositions which are useful as medical treatment for those conditions for which metronidazole is useful in treating.

7 Claims, No Drawings

METRONIDAZOLE PHOSPHATE AND SALTS

CROSS REFERENCE TO RELATED APPLICATIONS

The compounds of the Formula I are derivatives of the antibiotic compound metronidazole which is disclosed in U.S. Pat. No. 2,944,061.

BRIEF DESCRIPTION OF THE INVENTION

The compounds of the Formula are chemical derivatives of metronidazole which are useful for treating those diseases which metronidazole is useful in treating. The compounds are water soluble and can be prepared in dosage forms that the insoluble metronidazole could not. Additionally the compounds exhibit chemical stability in solutions.

DETAILED DESCRIPTION OF THE INVENTION

The novel compounds of the present invention are represented by the formula:

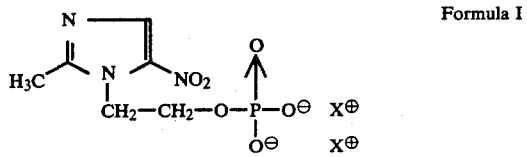

Formula I $X^\oplus$, a pharmacologically acceptable cation can be, for example H, Na, K, Li, ½ Ca, ½ Mg, ⅓ Al, ⅓ Fe, ½ Fe, NH$_4$, organic amines such as long chain primary amines, e.g., decyl-, lauryl-, myristyl-, palmityl- or stearyl-amine, amines which yield crystalline salts with organic acid, e.g., dicyclohexylamine, piperazine, benzylhydrylamine, amantadine, or tris(hydroxymethyl)aminomethane.

Starting with metronidazole of the formula:

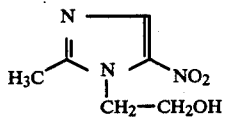

the compounds of the Formula I are prepared as follows:

A reaction mixture of metronidazole (1 mole), 2-cyanoethyl phosphate (2 mole), and dicyclohexylcarbodiimide (5 mole) in anhydrous pyridine is left at room temperature for two days. A stock solution of dicyclohexylcarbodiimide in anhydrous pyridine is made from barium 2-cyanoethyl phosphate dihydrate by passing an aqueous suspension through a cationic exchange column (H+ resin) and subsequent evaporation of water. After two days, dicyclohexylurea is precipitated out by adding water to the reaction mixture and filtered off. The filtrate is then concentrated and subject to silica gel liquid chromatography. Diphosphate ester thus obtained is hydrolyzed in KOH solution, carefully maintaining the pH of the reaction mixture at 10-11. After neutralizing the mixture with hydrochloric acid solution, the solvent is completely evaporated. The methanol extract is then evaporated and the remaining solid is recrystallized twice with 95% ethanol to provide the potassium salt.

The potassium salt of metronidazole phosphate thus obtained is dissolved in distilled water and eluted through a cationic exchange column (H+ resin). Free phosphoric acid of metronidazole dihydrogen phosphate ester is resulted upon evaporation of water. For the salts of organic amines, the phosphoric acid in an organic solvent (e.g., ether) is titrated with calculated amount of the amines in ether. The salts are obtained as precipitates. In case of the inorganic salts, the titration is carried out in distilled water and the water is evaporated. For both cases, the salts are recrystallized in a proper solvent system, if necessary.

The sodium and ammonium salts can be prepared in the same manner as the potassium salt by substituting sodium hydroxide or ammonium hydroxide for the potassium hydroxide. The Li, Ca, Mg, Al and Fe salts are prepared from the potassium salt by adding the appropriate reagent to a solution of the potassium salt, i.e., addition of aluminum chloride or aluminum nitrate to a solution of potassium metronidazole phosphate will give aluminum metronidazole phosphate. The amine salts can be prepared from metronidazole phosphate by adding one or two moles of the appropriate amine to one mole of metronidazole phosphate and collecting the precipitated metronidazole phosphate amine salt. The free acid of metronidazole phosphate can be prepared from potassium metronidazole phosphate by passing the salt through a cationic exchange resin (H+ resin) and evaporating the water.

The following examples are illustrative of the process and products of the present invention but are not to be construed as limiting.

EXAMPLE 1

Metronidazole Phosphate Dipotassium Salt

A stock solution of 1.0 M 2-cyanoethyl phosphate in anhydrous pyridine is prepared by suspending 16.16 gm. of 2-cyanoethyl phosphate, barium salt dihydrate in 160 ml. of water containing 70 ml. of Dowex 50W (20–50 mesh; H+ form) cationic exchanger. The suspension is stirred to effect solution. The solution is poured into a glass column (3.0 cm 1D×50 cm length) containing another 50 ml. of the same resin. The column is eluted with 300 ml. of water. The eluent plus 30 ml. of anhydrous pyridine is evaporated at 40° C. under reduced pressure. The residue is further dried twice by the addition of 200 ml. of anhydrous pyridine. The residue is transferred to a 50 ml. volumetric flask and anhydrous pyridine added to make 50 ml. 3.423 gm. of metronidazole (0.02 mole) and 40 ml. of the above stock solution of 2-cyanoethyl phosphate (0.04 mole) are mixed in a one liter round-bottom flask. The reaction mixture is concentrated at 40° C. under vacuum. The mixture is dried two more times, each with 150 ml. of anhydrous pyridine.

20.6 Gm. of N,N'-dicyclohexylcarbodiimide (DCC; Aldrich; MW-206.33; 0.1 mole) dissolved in 180 ml. of anhydrous pyridine is added and the stopper of the flask is wrapped with PARAFILM and the reaction mixture kept in the dark at low humidity.

After 48 hours 50 ml. of water is added to the reaction mixture and the pyridine evaporated under vacuum at 40° C. Another 300 ml. of water is added to the residue and let stand at room temperature for two hours. The crystalline N,N'-dicyclohexylurea is filtered off. 60 Ml. of Dowex 50W-X8 resin (H+ form) is suspended in the filtrate. The suspension is stirred for 20 minutes at room temperature and the resin filtered off. The filtrate is concentrated to approximately 20 ml. under vacuum at 40°.

The reaction mixture is injected into three consecutive silica gel columns (Size C—Silica gel 60 prepacked columns by EM Regeants). The LC columns are eluted with a mobile phase made of methanol (100 volume), water (2) and acetic acid (1). The eluent is monitored continuously by letting the flow pass through a flow cell of 0.5 cm. thickness in a spectrophotometer (Beckman DB-G) with the wavelength set at 390 nm. The fraction of the eluent between 1.30 and 2.00 l. is collected and the solvent evaporated.

To the oil obtained, 20 ml. of water is added and the solution slowly titrated with 31.0 ml. of 1.0N—KOH over a period of 30 min. at 45° maintaining the pH at 10-11. The solution is kept at 45° for 15 minutes. The solution is neutralized with 1N-HCl. The water evaporated under vacuum at 45°. The solid residue is extracted with 40 ml. of methanol. After evaporating the methanol, the solid residue is twice recrystallized with 3A-alcohol.

Analysis: Calc'd. for $C_6H_8N_3O_6K_2P.1.35H_2O$: C, 20.50; H, 3.07; N, 11.95; O, 33.45; K, 22.24; P, 8.81. Found: C, 20.07; H, 3.14; N, 10.76; K, 23.04.

EXAMPLE 2

Metronidazole Phosphate Disodium Salt

Following the procedure of Example 1 but substituting sodium hydroxide for the potassium hydroxide one can prepare metronidazole phosphate disodium salt.

Similarly by substituting ammonium hydroxide for potassium hydroxide in Example 1, one can prepare metronidazole phosphate ammonium salt.

EXAMPLE 3

Metronidazole Phosphate

Metronidazole phosphate potassium salt is dissolved in water and eluted through a cationic exchange column such as Dowex or Amberlite. The eluate is collected and evaporated to give metronidazole phosphate.

EXAMPLE 4

Metronidazole Phosphate Aluminum Salt

Metronidazole phosphate potassium salt is dissolved in water. To this solution is added a solution of aluminum chloride in water. The solution is stirred and the water is evaporated to give metronidazole phosphate aluminum salt.

EXAMPLE 5

Metronidazole Phosphate Amine Salts

To a slurry of metronidazole phosphate in solvent is added the appropriate amine in an organic solvent and the mixture is triturated. The amine salts are obtained as precipitates.

The compounds of the Formula I have antibiotic activity and can be used for treating those conditions for which metronidazole is known to be useful.

The dosage of the compound of the Formula I for antibiotic purposes is from about 0.5 to about 10.0 mg./kg. body weight of the patient. The compounds of the Formula I are conveniently prepared in 10, 50, 100, 250 and 500 mg. dosage units for administration 1 to 4 times a day. Preferred dosages are from 1 to 5 mg./kg. body weight of the patient up to four doses per day.

The compounds are administered orally, parenterally, vaginally and rectally for systemic action.

The compositions of the present invention are presented for administration to humans and animals in unit dosage forms, such as tablets, capsules, pills, powders, granules, sterile parenteral solutions or suspensions, and oral solutions or suspensions and oil-water emulsions containing suitable quantities of a compound of Formula I or its pharmacologically acceptable salts.

Pharmaceutical dosage unit forms are prepared in accordance with the subsequent general specific descriptions to provide from about 10 mg. to about 500 mg. of the essential active ingredient per dosage unit form (preferred 100-250 mg.).

Oral pharmaceutical dosage forms are either solid or liquid. The solid dosage forms are tablets, capsules, granules, and bulk powders. Types of oral tablets are, for example, compressed (including chewable and lozenge), tablet triturates, enteric-coated, sugar-coated, film-coated, and multiple compressed. Capsules are either hard or soft elastic gelatin. Granules and powders are either effervescent or non-effervescent.

Pharmaceutically acceptable substances utilized in compressed tablets are binders, lubricants, diluents, disintegrating agents, coloring agents, flavoring agents, flow inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose polymer. Multiple compressed tablets are compressed tablets made by more than one compression cycle utilizing the pharmaceutically acceptable substances previously mentioned. Coloring agents are utilized in the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25-50%), acacia mucilage (10-20%), gelatin solution (10-20%), sucrose and starch paste. Lubricants include, for example, talc, starch, magnesium or calcium stearate, lycopodium and stearic acid. Diluents include, for example, lactose, sucrose, starch, kaolin, salt, mannitol and dicalcium phosphate. Disintegrating agents include, for example, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, and artificial sweetening agents such as sodium cyclamate and saccharine, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate and polyoxyethylene laural ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets, include, for example, dextrin and gelatin. The second layer, an opaque zone, includes, for example, starch, talc, calcium carbonate, magnesium oxide and magnesium carbonate. The third layer, a translucent zone, includes, for example, sucrose. The fourth layer, a glaze, includes, for example, beeswax, carnauba wax, or a mixture of these waxes. Film-coatings include, for example, hydroxyethylcellulose, sodium carboxymethylcellulose, polyethylene glycol 4000 and cellulose acetate phthalate.

Hard gelatin capsules, sizes 5 through 1000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastro-intestinal tract, polyvinyl alcohol, ethyl cellulose and mixtures of beeswax, carnauba wax or bayberry wax with glyceryl monostearate.

Soft elastic gelatin capsules contain sufficient glycerine so that they are permanently flexible. Pharmaceutically acceptable liquid diluents used in soft elastic gelatin capsules are those which do not dissolve or harm the capsule and which are non-toxic, including, for example, corn oil, cottonseed oil, polysorbate 80, DMA and triacetin.

Pharmaceutically acceptable substances utilized in non-effervescent granules, for solution and/or suspension, include diluents, wetting agents, flavoring agents and coloring agents. Examples of diluents, wetting agents, flavoring agents and coloring agents include those previously exemplified.

Pharmaceutically acceptable substances utilized in effervescent granules and powders include organic acids, a source of carbon dioxide, diluents, wetting agents, flavoring agents and coloring agents.

Examples of organic acids include, for example, citric acid and tartaric acid. Sources of carbon dioxide include, for example, sodium bicarbonate and sodium carbonate. Examples of sweetening agents include, for example, sucrose, calcium cyclamate and saccharine. Examples of diluents, wetting agents and coloring agents include those previously exemplified.

Bulk powders have the compound of the Formula I uniformly dispersed throughout a pharmaceutically acceptable powdered carrier diluent. Examples of the diluent include those previously exemplified.

The individual solid pharmaceutical dosage forms, tablets and capsules, are packaged individually, unit-dose, or in quantity, multiple-dose containers, for example, bottles of 50, 100, 500, 1000, or 5000.

The amount of compound of the Formula I analog per dose unit is adjusted so that it provides the patient with an effective amount. The exact dose depends on the age, weight and condition of the patient or animal as is known in the art. For example, tablets and capsules are given in sufficient number and frequency to obtain the desired pharmacological effect.

The sustained release tablets and capsules provide an effective amount upon ingestion and continue to release a sufficient amount of the active material to keep the concentration at an effective level for increased periods of time, for example, 12 hours.

Non-effervescent granules and powders are packaged in predetermined amounts, such that when reconstituted with a specified quantity of an appropriate liquid vehicle, usually distilled water, a solution and/or suspension results, providing a uniform concentration of the compound of the Formula I after shaking, if necessary. The concentration of the solution is such that a teaspoonful (5 ml.), a tablespoonful (one-half ounce or 15 ml.) or a fraction or a multiple thereof will provide an effective amount to produce the desired pharmacological effect. The exact dose depends on the age, weight and condition of the patient or animal, as is known in the art.

Effervescent granules and powders are packaged either in unit-dose, for example, tin foil packets, or in bulk, for example, in 4 oz. and 8 oz. amounts, such that a specific amount, either a unit-dose or, for example, a teaspoonful, tablespoonful, or a fraction or a multiple thereof of bulk granules, when added to a specific amount of liquid vehicle, for example, water, yields a container of liquid dosage form to be ingested. The concentration of the active material in the granules is adjusted so that a specified amount when mixed with a specific amount of water yields an effective amount of the active material and produces the desired pharmacological effect. The exact amount of granules to be used depends on age, weight and condition of the patient as is known in the art.

Liquid oral dosage forms include, for example, aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water (o/w) or water-in-oil (w/o).

Elixirs are clear, sweetened, hydroalcoholic preparations. Pharmaceutically acceptable substances utilized in elixirs include, for example, solvents. Syrups are concentrated aqueous solutions of a sugar, for example, sucrose, and may contain a preservative. An emulsion is a two-phase system in which one liquid is dispersed in the form of small globules throughout another liquid. O/w emulsions are much preferred for oral administration over w/o emulsions. Pharmaceutically acceptable substances utilized in emulsions are non-aqueous liquids, emulsifying agents and preservatives. Suspensions utilize pharmaceutically acceptable suspending agents and preservatives. Pharmaceutically acceptable substances utilized in non-effervescent granules, to be reconstituted into a liquid oral dosage form, include, for example, diluents, sweeteners, and wetting agents. Pharmaceutically acceptable substances utilized in effervescent granules, to be reconstituted into a liquid oral dosage form, include, for example, organic acids and a source of carbon dioxide. Coloring and flavoring agents are utilized in all of the above dosage forms.

Solvents include, for example, glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include, for example, mineral oil and cottonseed oil. Examples of emulsifying agents include for example, gelatin, acacia, tragacanth, bentonite, and surfactants such as polyoxyethylene sorbitan monooleate. Suspending agents include, for example, sodium carboxymethylcellulose, pectin, tragacanth, Veegum and acacia. Diluents include, for example, lactose and sucrose. Sweetening agents include, for example, sucrose, syrups, glycerin, and artificial sweetening agents such as sodium cyclamate and saccharin. Wetting agents include, for example, propylene glycol monostearate, sorbitan monooleate, diethylene glycol monolaurate and polyoxyethylene lauryl ether. Organic acids include, for example, citric and tartaric acid. Sources of carbon dioxide include, for example, sodium bicarbonate and sodium carbonate. Coloring agents include, for example, any of the approved, certified water soluble FD and C dyes, and mixtures thereof. Flavoring agents include, for example, natural flavors extracted from plants such as fruits, and synthetic blends of compounds which produce a pleasant taste sensation.

The concentration of the compound of the Formula I throughout the solutions must be uniform. Upon shaking, the concentration of the compound of the Formula I throughout the emulsions and suspensions must be uniform.

The concentration of the compound of the Formula I is adjusted so that a teaspoonful (5 ml.), a tablespoonful (one-half ounce or 15 ml.) or a fraction or multiple thereof, will provide an effective amount to produce the desired pharmacological effect. The exact dose depends on the age, weight and condition of the patient or animal as is known in the art.

The liquid oral dosage forms may be packaged, for example, in unit-dose sizes of 5 ml. (teaspoonful), 10 ml., 15 ml. (tablespoonful) and 30 ml. (one ounce), and multiple dose containers, including, for example, 2 oz., 3 oz., 4 oz., 6 oz., 8 oz., pint, quart, and gallon sizes.

Parenteral administration includes intravenous, subcutaneous, intramuscular, and the like.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or non-aqueous.

Pharmaceutically acceptable substances utilized in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutical necessities.

Examples of aqueous vehicles include Sodium Chloride Injection, Ringers Injection, Isotonic (5 percent) Dextrose Injection, Sterile Water for Injection, Dextrose and Sodium Chloride Injection and Lactated Ringers Injection. Non-aqueous pareneteral vehicles include fixed oils of vegetable origin, for example, cottonseed oil, corn oil, sesame oil and peanut oil. Antimicrobial agents in bacteriostatic or fungistatic concentrations must be added to parenteral preparations packaged in multiple-dose containers (vials) which include phenol or cresols, mercurials, benzyl alcohol, chlorobutanol, methyl and propyl p-hydroxybenzoic acid esters, thimerosal, benzalkonium chloride and benzethonium chloride. Isotonic agents include, for example, sodium chloride and dextrose. Buffers include, for example, phosphate and citrate. Antioxidants include, for example, sodium bisulfite. Local anesthetics include, for example, procaine hydrochloride. Suspending and dispersing agents include, for example, sodium carboxymethylcellulose, hydroxypropyl methylcellulose and polyvinylpyrrolidone. Emulsifying agents include, for example, Polysorbate 80 (Tween 80). A sequestering or chelating agent of metal ions include, for example EDTA (ethylenediaminetetraacetic acid). Pharmaceutical necessities include, for example, ethyl alcohol, polyethylene glycol and propylene glycol for water miscible vehicles and sodium hydroxide, hydrochloric acid, citric acid or lactic acid for pH adjustment.

The concentration of the pharmaceutically active ingredient is adjusted so that an injection, for example, 0.5 ml., 0.1 ml., 2.0 ml., and 5.0 ml. or an intraarterial or intraveneous infusion, for example, 0.5 ml./min., 1.0 ml./min., 1.0 ml./min., and 2.0 ml./min. provides an effective amount to produce the desired pharmacological effect. The exact dose depends on the age, weight and condition of the patient or animal as is known in the art.

The unit-dose parenteral preparations are packaged, for example in an ampul or a syringe with a needle. The multiple-dose package, for example, is a vial.

All preparations for parenteral administration must be sterile, as is known and practiced in the art.

Illustratively, intravenous or intraarterial infusion of a sterile aqueous solution containing an active material is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules, tablets for systemic effect.

Rectal suppositories as used herein mean solid bodies of insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 gm.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantity, multiple dose, for example, 2, 6, or 12.

The pharmaceutically therapeutically active compounds of the Formula I are administered orally, parenterally or rectally in unit-dosage forms or multiple dosage forms. Unit-dose forms as used in the specification and claims refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral), individually packaged tablet or capsule (oral-solid) or individually packaged teaspoonful or tablespoonful (oral-liquid). Unit-dose forms may be administered in fractions or multiples thereof. A multiple-dose form is a plurality of identical unit-dosage forms packaged in a single container to be administered in segregated unit-dose form. Examples of multiple-dose forms include vials (parenteral), bottles of tablets or capsules (oral solid) or bottles of pints or gallons (oral-liquid). Hence, multiple-dose form is a multiple of unit-doses which are not segregated in packaging. The specifications for the unit-dosage form and the multiple-dosage form are dictated by and directly dependent on (a) the unique characteristics of the therapeutically active compound and the particular therapeutic effect to be achieved and (b) the limitations inherent in the art of compounding such a therapeutically active compound for therapeutic or prophylactic.

In addition to the administration of a compound of Formula I as the principal active ingredient of compositions for the treatment of the conditions described herein, the said compound can be included with other types of compounds to obtain advantageous combinations of properties. Such combinations include a compound of Formula I with other analgesics such as aspirin, phenacetin, acetaminophen, propoxyphen, pentazocine, codeine, meperidine, oxycodone, mefenamic acid, and ibuprofen; muscle relaxants such as methocarbamol, orphenadrine, carisopropdol, meprobamate, chlorphenesin carbamate, diazepam, chlordiazepoxide, and chlorzoxazone; analeptics such as caffeine, methylphenidate and pentylenetetrazole; corticosteroids such as methylprednisolone, prednisone, prednisolone and dexamethasone, antihistamines such as chlorpheniramine, cyproheptadine, promethazine and pyrilamine.

EXAMPLE 6

Tablets

One thousand oral tablets, each containing 250 mg. of potassium metronidazole phosphate are prepared from the following types and amounts of materials:

Potassium medronidazole phosphate: 250 g.
Lactose: 50 g.
Corn starch: 50 g.
Calcium stearate: 2.5 g.
Light liquid petrolatum: 5 g.

The ingredients are thoroughly mixed and slugged. The slugs are broken down by forcing through a number sixteen screen. The resulting granules are then compressed into tablets, each containing 250 mg. of potassium metronidazole phosphate.

The foregoing tablets are useful for treatment of trichomoniasis by the oral administration of 1 tablet every six hours.

EXAMPLE 7

Oral Syrup

One thousand ml. of an aqueous suspension for oral use, containing in each 5 ml. dose, 100 mg. of potassium metronidazole phosphate is prepared from the following types and amounts of ingredients:

Potassium metronidazole phosphate: 20 g.
Citric acid: 2 g.
Benzoic acid: 1 g.
Sucrose: 700 g.
Tragacanth: 5 g.
Lemon oil: 2 ml.

Deionized water q.s.: 1000 ml.

The citric acid, benzoic acid, sucrose, tragacanth, and lemon oil are dispersed in sufficient water to make 850 ml. of solution. The potassium metronidazole phosphate is stirred into the syrup until uniformly distributed. Sufficient water is added to make 1000 ml.

The composition so prepared is useful in the treatment of amebiasis in adult humans at a dose of 1 teaspoonful 4 times a day.

EXAMPLE 8

Parenteral Solution

A sterile aqueous solution for intramuscular use, containing in 1 ml. 400 mg. of potassium metronidazole phosphate is prepared from the following types and amounts of materials:

Potassium metronidazole phosphate: 400 g.
Lidocaine hydrochloride: 4 g.
Methylparaben: 2.5 g.
Propylparaben: 0.17 g.
Water for injection q.s.: 1000 ml.

The ingredients are dissolved in the water and the solution sterilized by filtration. The sterile solution is filled into vials and the vials sealed.

The composition so prepared is useful in the treatment of trichomoniasis in adult humans at a dose of 1 cc injected I.M. every 8 hours.

EXAMPLE 9

Suppository, Rectal

One thousand suppositories, each weighting 2.5 g. and containing 50 mg. of potassium metronidazole phosphate are prepared from the following types and amounts of ingredients:

Potassium metronidazole phosphate: 50 g.
Propylene glycol: 162.5 g.
Polyethylene glycol 4000 q.s.: 2300 g.

The potassium metronidazole phosphate is added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The suppositories are useful in the treatment of amebiasis in adult humans by the insertion rectally of 1 suppository every six hours.

EXAMPLE 10

Compositions for similarly prepared following the procedure of the preceding Examples 6 through 9 substituting an equimolar amount each of metronidazole phosphate, metronidazole phosphate sodium salt, metronidazole phosphate amine salts, metronidazole phosphate aluminum salt and the like for the potassium metronidazole phosphate of the Example.

We claim:

1. A compound of the formula:

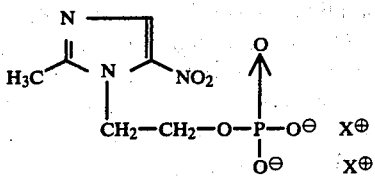

wherein X⊕ is a pharmacologically acceptable cation.

2. A compound according to claim 1 wherein X is potassium.

3. A pharmaceutical composition comprising a pharmaceutically effective amount of a compound of the formula:

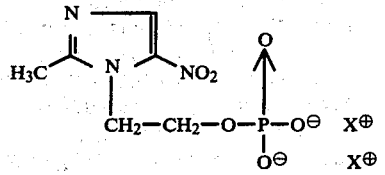

wherein X⊕ is a pharmacologically acceptable cation, in association with a pharmaceutical carrier.

4. A composition according to claim 3 in unit dosage form wherein the compound is present in a concentration of from about 10 to about 500 mg.

5. A process of antibiotic treatment comprising the administration to a subject of a therapeutic amount of a compound of the formula:

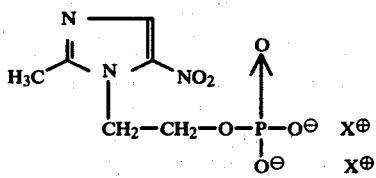

wherein X⊕ is a pharmacologically acceptable cation, in association with a pharmaceutical carrier.

6. The process of claim 5 wherein the amount of compound administered is from about 2 to about 6 mg./kg. body weight of the subject.

7. The process of claim 6 wherein X is potassium.

* * * * *